(12) United States Patent
Hendriks et al.

(10) Patent No.: US 8,697,442 B2
(45) Date of Patent: *Apr. 15, 2014

(54) ISOLATION OF CELLS

(75) Inventors: Jeanine Anna Alphonse Hendriks, Amerongen (NL); Adetola Bamidele Adesida, Manchester (GB)

(73) Assignee: Cellcotec B.V., Bilthoven (NL)

( * ) Notice: Subject to any disclaimer, the term of this patent is extended or adjusted under 35 U.S.C. 154(b) by 41 days.

This patent is subject to a terminal disclaimer.

(21) Appl. No.: 12/439,145

(22) PCT Filed: Aug. 31, 2007

(86) PCT No.: PCT/NL2007/050431
§ 371 (c)(1),
(2), (4) Date: Nov. 10, 2009

(87) PCT Pub. No.: WO2008/026929
PCT Pub. Date: Mar. 6, 2008

(65) Prior Publication Data
US 2010/0144036 A1    Jun. 10, 2010

(30) Foreign Application Priority Data

Aug. 31, 2006   (EP) .................................. 06076645

(51) Int. Cl.
*C12N 5/00*   (2006.01)
*C12N 5/02*   (2006.01)

(52) U.S. Cl.
USPC ......................................... 435/381; 435/378

(58) Field of Classification Search
None
See application file for complete search history.

(56) References Cited

U.S. PATENT DOCUMENTS

2003/0224518 A1*   12/2003   Adkisson, IV ................ 435/375
2010/0047316 A1*   2/2010    Hendriks ...................... 424/425

OTHER PUBLICATIONS

Glade et al. Enzymatic Isolation of Chondrocytes from Immature Rabbit Articular Cartilage and Maintenance of Phenotypic Expression in Culture. 1991. Journal of Bone and Mineral Research. vol. 6, No. 3, pp. 217-226.*
Roberts et al., Autologous chondrocyte implantation for cartilage repair: monitoring its success by magnetic resonance imaging and histology. Nov. 13, 2002. Arthritis Research and Therapy. vol. 5, No. 1, pp. R60-R73.*
Judas et al. Chondrocyte Viability in Freash and Frozen Large Human Osteochondral Allografts: Effect of Cryoprotective Agents. Transplantation Proceedings. 2007. vol. 39, pp. 2531-2534.*
De Angelis et al., The Journal of Physiology (1999) 518(Pt. 1):187-194.
Gartland et al., Bone (2005) 37(4):530-544.
International Search Report for PCT/NL2007/050431, mailed on Feb. 5, 2008, 2 pages.
Kolettas et al., Journal of Cell Science (1995) 108(Pt. 5):1991-1999.
Jakob et al., "Enzymatic Digestion of Adult Human Articular Cartilage Yields a Small Fraction of the Total Available Cells," Connective Tissue Research (2003) 44:173-180.
Lin et al., "The Chondrocyte: Biology and Clinical Application," Tissue Eng. (2006) 12(7):1971-1984.

* cited by examiner

*Primary Examiner* — Anne Gussow
*Assistant Examiner* — Channing S Mahatan
(74) *Attorney, Agent, or Firm* — Morrison & Foerster LLP

(57) ABSTRACT

The invention relates to a method for isolating cells from a tissue sample. In preferred embodiments, chondrocytes are isolated from cartilage tissue in a shorter time than hitherto considered possible.

17 Claims, 3 Drawing Sheets

ISOLATION OF CELLS

CROSS-REFERENCE TO RELATED APPLICATIONS

This application is the national phase of PCT application PCT/NL2007/050431 having an international filing date of 31 Aug. 2007, which claims benefit of European patent application No. 06076645.8 filed 31 Aug. 2006. The contents of the above patent applications are incorporated by reference herein in their entirety.

FIELD OF THE INVENTION

The invention relates to a method for isolating cells from a tissue sample.

BACKGROUND OF THE INVENTION

Cartilage disorders are highly debilitating disorders including, for instance, articular cartilage trauma, meniscus injury, chondrogenesis disorders and arthritis. There are at present no optimal therapies available for treating these disorders. Cartilage tissue is neither innervated nor penetrated by the vascular or lymphatic systems and it is generally believed that due to this lack of a vasculature, damaged cartilage tissue does not receive sufficient or proper stimuli to elicit a repair response. Repair of arthritic joints thus requires orthopaedic surgery to replace the worn-out joints by a prosthesis or by a biological graft. Particularly arthritis is an enormous medical and economic problem.

Current approaches for cartilage repair rely on removal of tissue debris, access to the wound healing system of bone by penetrating the subchondral bone plate, and tissue transplantation and cell based therapies. Current clinical therapies typically involve autologous cells. Examples of such therapies are autologous chondrocytes implantation (ACI) and mosaicplasty (also known as autologous osteochondral grafts). Due to severe drawbacks, both therapies can currently only address a limited share of the cartilage repair market.

For mosaicplasty, a major disadvantage is the limitation to small defects due to limited availability of donor tissue for transplantation. For ACI, drawbacks include the necessity to perform two surgical operations, one for harvesting cartilage tissue, and another for implantation of in vitro expanded chondrocytes obtained from the harvested cartilage tissue. Apart from the fact that high costs are involved, the ACI process is long since in vitro cell expansion is necessary, during which cartilage cells de-differentiate, and lose their phenotype. Hence, a long rehabilitation of several months is needed following the surgical implantation procedure for the cells to regain their original phenotype. Only then true cartilage repair can commence.

Recently, a second generation ACI has been developed involving autologous chondrocytes in a biomaterial matrix. This technique solves some of the problems of ACI, particularly the long and open surgical procedure that was required in ACI. However, important drawbacks remain: two surgical procedures have to be carried out, involving high costs and long rehabilitation. One of the reasons why two surgical procedures have to be carried out is that the current processes for isolating chondrocytes from a tissue sample extracted from the patient takes a long time.

Hyaline cartilage, the most abundant form of cartilage, is glass smooth, glistening and bluish white in appearance and of this form of cartilage articular cartilage is the most common. Articular cartilage covers the ends of long bones of synovial joints. It is characterized by a particular structural organization, consisting of chondrocytes embedded in an extracellular material, typically referred to as "cartilage matrix", which is an extracellular matrix rich in proteoglycans, collagen fibrils, other proteins, and water. Chondrocytes are the only cell type found in normal articular cartilage but contribute less then 2% of the wet weight in human healthy adult cartilaginous tissue.

The extracellular matrix of cartilage tissue consists predominantly of cartilage specific proteoglycan molecules with highly negatively charged sulphated glycosaminoglycan (GAG) side chains, as well as type II collagen fibrils. The GAG side chains are able to bind water molecules, thereby sequestering water and generating an internal swelling pressure within the cartilage matrix. These hydrogel-like properties are essential for the interstitial fluid flow patterns observed inside the matrix during functional loading of cartilage, at which point water is forced out of the tissue to an amount that allows the negatively charged GAG chains to repel each other. Upon release of the compressive load, water is imbibed back into the tissue matrix. The collagenous network, together with water bound GAG, enables articular cartilage to withstand large compressive loads which gives the tissue its unique function in synovial joints: smooth and pain-free articulation, spreading of the applied load onto the subchondral bone and absorbing mechanical shocks.

In normal cartilaginous tissue, proteoglycans are slowly but continuously turned over, the degraded molecules are released from the cartilage and are replaced by newly synthesized components. It is the coordinate control of synthesis and degradation of the matrix components by the chondrocytes that maintain normal cartilage.

After a tissue sample of the cartilage of the patient has been extracted, the chondrocytes present in that sample have to be isolated from the extracellular matrix before they can be expanded and implanted with the aim of repairing a cartilage tissue defect. Enzymatic liberation of cells located within an extracellular matrix, requires diffusion of the enzyme to the substrate (e.g. collagen), digestion of collagen, and liberation of the cells.

Known procedures for chondrocyte isolation are carried out by incubating a cartilage tissue sample with a solution of collagenase for a period of from 16 to 22 hours. The current belief is that shorter incubation times do not produce sufficient cell yields for expansion and tissue repair purposes, whereas longer exposure to collagenase is believed to compromise cell viability. The shortest incubation time described in the art appears to be 2 hours (Jakob et al., Connective Tissue Research, 44 (2003), 173-180). Digestion was never terminated before 2 hours.

SUMMARY OF THE INVENTION

The present invention provides a method for isolating cells, preferably chondrocytes, from a tissue sample which is considerably shorter than prior art methods. Thus, unlike the known isolation procedures, a method for isolating cells according to the invention can be completed within the usual duration of a surgical procedure for repairing a cartilage defect. Surgical procedures for cartilage defect treatments usually last between 30 and 90 minutes. It has now been shown, surprisingly, that a substantial and sufficient number of cells can be isolated within 30 minutes, or even 10 minutes.

The current view in the art is that a high number of chondrocytes is required for use in cartilage defect repair: typically at least 1 million chondrocytes for repair of a defect having a volume of 1 milliliter. Surprisingly, it has now been shown that a cell number of less than 1 million chondrocytes may be sufficient to apply to a cartilage tissue defect of a volume of 1 milliliter to achieve cartilage formation.

The present invention thus relates to a method for isolating cells from a tissue sample comprising subjecting the tissue sample to a digestion enzyme for a period of less than 2 hours, and harvesting the isolated cells.

Although it is preferred that chondrocytes are isolated from a cartilage tissue sample, particularly intended for use in cartilage tissue repair, the invention also contemplates isolation of other types of cells from other types of tissue samples. Examples of primary cells that may be isolated in accordance with the invention include chondrocytes, nerve cells, osteoblasts, osteoclasts, hepatocytes, cardiomyocytes, myocytes, Schwann cells or urothelial cells. For use in tissue repair, the type and source of the primary cells may be chosen dependent on the type of tissue that is intended to be repaired.

DETAILED DESCRIPTION OF THE INVENTION

Figure 1:
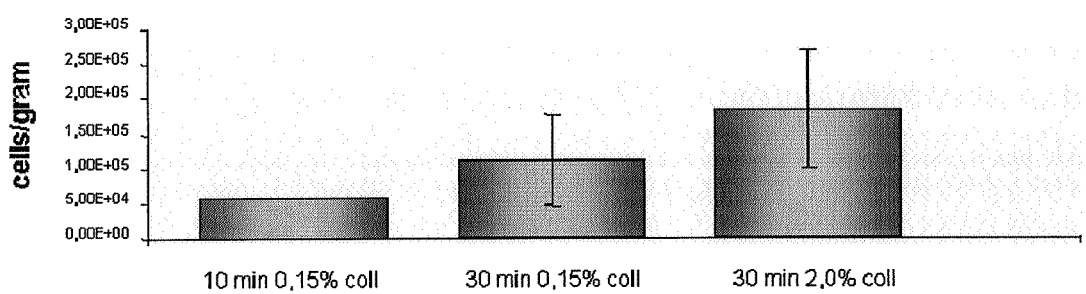
FIG. 1 is a graph showing the effect of collagenase concentration and time of digestion on production of viable cells from cartilage.

The following overview gives examples of how cell types of primary cells may be selected with a view to repair of a specific tissue type.

| Repair tissue | Primary cell source |
|---|---|
| Bone | osteoblasts from trabecular bone in long bone, pelvic bone, clavicula, compact, subchondral bone |
| Cartilage | Chondrocytes derived from nose, knee or hip joint, elbow, ear, ankle or trachea cartilage, isolated chondron |
| Liver | Hepatocytes from liver |
| Heart, Heart valves | Cardiomyocytes from heart muscle, vascular myofibroblasts form vascular tissue in the heart |
| Muscle | Myocytes from smooth muscle |
| Nerve | Schwann cells, neural cells from epineurial tubes |
| Bladder | Urothelial cells from urological tract |
| Intestine | Cells from jejunum, duodenum |
| Ligaments and Tendons | Cells from cruciate ligaments or tendon |
| Hair | Cells from hair follicle, such as dermal papilla cells, outer root sheath or matrix epithelial cells |

Preferably, the primary cells are of a cell type that naturally occurs in the tissue that will be repaired. In a preferred embodiment, chondrocytes are isolated from a sample of articular cartilage, e.g. for repair of cartilage defects.

Prior to subjecting the tissue sample to the digestion enzyme, a method according to the invention may comprise mincing of the tissue sample to obtain smaller fragments of the tissue, preferably approximately 0.5 to 2 mm in diameter, more preferably about 1 mm. Mincing may be performed by any suitable method, for instance using scissors, one or more razor blades (a set of parallel razorblades can be used to make slices, or two such sets can be used to make cubes), a scalpel, straining through a steel or nylon mesh screen or sieve, or disaggregating it through a needle.

In a preferred embodiment, the tissue sample is subjected to a treatment to increase extracellular matrix permeability prior to subjecting it to the digestion enzyme. It is contemplated that one of the factors determining the efficiency of the isolation of cells from the tissue sample, is the access of the digestion enzyme to the cells and extracellular matrix in the sample. The permeability of cartilage is determined by chemical and mechanical factors, water and proteoglycan interactions. It is preferred that the treatment to increase extracellular matrix permeability, particularly for cartilage tissue, comprises increasing repulsive forces between glycosaminoglycans present in the extracellular matrix. In a preferred embodiment, this treatment comprises contacting the tissue sample to an acid, a base, dimethyl sulfoxide (DMSO), cathepsin, glycerol, or cations, or any other agent which may increase the Donan osmotic pressure of the extracellular matrix or cause the extracellular matrix to swell, prior to subjecting it to the digestion enzyme.

Suitable examples of cations include $Na^+$, $K^+$, $NH_4^+$, $Pb^{2+}$, $Mg^{2+}$, $Zn^{2+}$, $Fe^{2+}$, $Cd^{2+}$, and $Cu^{2+}$. These may for instance be introduced in the form of their chloride salts, preferably in a concentration between 10 mM and 2 M. A suitable acid is for instance hydrochloric acid, preferably in a concentration of 10-100mM, resulting in a decrease of the pH of the extracellular matrix. Dimethylsulfoxide (DMSO) and glycerol may be used in a concentration between 5 and 30% v/v. Other suitable agents for this step include disodium ethylenediaminetetraacetate (EDTA) or ethyleneglycolbis (β-aminoethyl ether) N,N'-tetraacetic acid (EGTA), both preferably used in a concentration of 0.01-0.1 M) or citrate in Tris buffer, pH 5.8 and 7.4, at 4° and 37°. After the permeability of the tissue is increased, the tissue sample may be washed with for instance phosphate buffered saline before subjecting it to a digestion enzyme.

The step of increasing permeability preferably lasts from 1 minute up to no more than 1 hour, preferably maintaining the total isolation time of the cells to be within the 2 hour range. It is preferably performed at a temperature between 17° C. and 37° C.

The tissue sample, possibly in the form of small fragments, is then incubated in a digestion solution. The digestion solution comprises one or more enzymes chosen from the group consisting of collagenases, pronases, dispases, trypsins, hyaluronidases, chondroitinases, elastases, and heparitinases. The type of enzyme will depend on the type of tissue used. It is also contemplated to use different enzymes sequentially or simultaneously. For cartilage, it is preferred that collagenase type II is used. A suitable amount of enzyme is for instance 0.05-20 wt. %, preferably below 10 wt. %, more preferably 0.15-2 wt. %, based on the weight of the digestion solution.

The conditions (e.g. pH and temperature) under which a method according to the invention is carried out will be chosen such that they are optimal for the cells that are being isolated and for the digestion enzyme and possible other agents used. To this end, the digestion solution may further comprise buffering agents which help to maintain the pH in the range which approximates physiological conditions. They are preferably present at concentration ranging from about 1 mM to about 100 mM. Suitable buffering agents for use in the present invention include both organic and inorganic acids and salts thereof such as citrate, succinate, tartrate, fumarate, gluconate, oxalate, lactate, acetate phosphate and borate buffers. Additionally, there may be mentioned, histidine, glycine and urea buffers and buffers such as Tris, MOPS and HEPES.

The digestion solution may further comprise such compounds as: chelating agents, e.g. diethylenetriaminepentacetic acid (DTPA), ethylenediaminetetraacetic acid (EDTA, e.g. as Versene™), ethylene bis(oxyethylenenitrolo)tetraacetic acid (EGTA); reducing agents, such as dithiotreitol, dithioerythritol, β-mercaptoethanol, glutathione, thioredoxin, cysteine, etc.; ions necessary for activation of the enzyme such as $CaCl_2$, $MgCl_2$, NaCl and/or KCl; and/or organic solvents or lipid/membrane modifying agents such as dimethyl sulfoxide (DMSO); nonionic detergents such as triton X-100; and/or osmoprotectants such as sucrose.

In accordance with the invention, the tissue sample is subjected to the digestion enzyme for a period of less than 2 hours. In a preferred embodiment, the tissue sample is subjected to the digestion enzyme for a period of less than 1 hour, more preferably for a period of at least 1 minute, more preferably from 5 minutes to 1 hour, and even more preferably for a period of from 10 to 30 minutes. It is further preferred that, if the method encompasses a pre-treatment to increase extracellular matrix permeability, the periods of time specified in this paragraph cover both the subjecting of the tissue sample to the digestion enzyme and the pre-treatment. As mentioned above, it is an important advantage of the invention that a method for isolating cells is provided that can be completed within the usual duration of a surgical procedure for repairing a tissue defect, such as a cartilage tissue defect.

The isolated cells may then be harvested in the usual manner, e.g. by filtration, washing, centrifuging, and/or magnetic bead extraction. During this step, the cells are separated from the digestion enzyme and possible other agents used, thereby effectively ending the digestion process. If desired, the digestion enzyme may be inactivated prior to this separation step, e.g. by adjustment of the pH.

Filtration may be carried out by pouring the cell suspension still comprising the digestion solution on a tissue culture grade filter. Subsequently, the cells may be washed, for instance by pouring phosphate buffered saline (PBS) onto the cells while they are still on the filter. Finally, the cells may be resuspended in a suitable medium.

Washing may be carried out by centrifuging the cell suspension still comprising the digestion solution and aspirating the supernatant, followed by resuspending the cells in a relatively large volume of PBS. The cells may then centrifuged again. This procedure can be repeated several times to achieve the desired degree of washing.

Isolation using magnetic beads may be carried out by adding magnetic beads coated with a general receptor (e.g. α5β1 integrin) or a suitable antibody, to the cell suspension still comprising the digestion solution. The cells will bind to the magnetic beads via their membrane expressed epitope (e.g. fibronectin). With the aid of a magnet, the beads with the cells attached thereto are concentrated to the bottom of a tube and the supernatant may be aspirated. The magnetic beads with the cells may be washed with e.g. PBS. This process can be repeated several times. Finally, the cells may be separated from the magnetic beads by trypsin treatment, competition by washing with epitope containing buffer (e.g. fibronectin) or washing with 1 mM to 10 mM aqueous HCl solution.

EXAMPLES

The invention will now be elucidated by the following, non-restrictive examples.

EXAMPLE I

Cartilage from human subjects was dissected to approximate 1×1 mm cubes, incubated in a 0.15% or 2% collagenase solution (type II collagenase, dissolved in DMEM, filter sterilized through 0.22 μm filter and supplemented with 10% V/V FBS; approximately 10 ml of collagenase suspension per g of cartilage) on an orbital-(xyz-)shaker at 37 ° C. and 5% $CO2$ for 10 or 15 min. Next, undigested cartilage was separated through a cell strainer, the cell suspension was centrifuged at 4° C., 300 g for 10-20 minutes, the supernatant was aspirated off, and the centrifugation was repeated 2 times. Next, cells were resuspended in chondrocyte medium and viable cells were counted using trypan blue staining. The results are shown in FIG. 1.

EXAMPLE II

Figure 2:
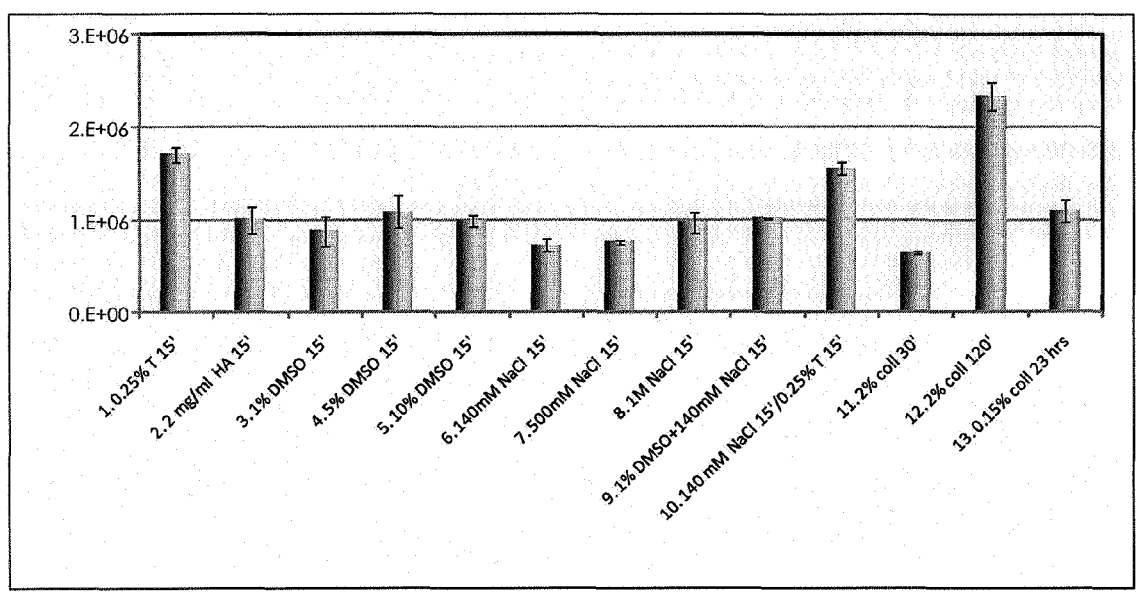
FIG. 2 is a graph showing the effect of a variety of digestion reaction conditions (shown in Table 1) on production of viable cells from cartilage.

Cartilage was retrieved from adult human cartilage biopsies (n=4) from the tibia. The cartilage was minced into ≤1 $mm^3$ pieces. Approximately 1 gram of cartilage per group was transferred to 50 ml tubes and the exact weight of cartilage was determined (table 1). Chondrocytes were isolated by means of different pretreatment as described in Table 1, immediately followed by collagenase type II (Worthington) digestion for 30 minutes. The digested suspension was filtered through a 100 μm mesh nylon filter and the resulting cell suspension was centrifuged at 300 g for 10 minutes at 4° C. The cell pellet was washed twice with phosphate buffered saline (PBS) and finally resuspended in 1 ml PBS. The number of cells and the number of dead cells were determined with a Burker-Turk counting chamber and Trypan blue staining. The results are summarized in Table 1 and FIG. 2.

TABLE 1

| treatment | total n cells | weight cartilage (g) | total n cells/g | sd | normalized to #11 |
|---|---|---|---|---|---|
| 1. 0.25% T 15' | 1.42E+06 | 0.83 | 1.71E+06 | 8.49E+04 | 2.63 |
| 2. 2 mg/ml HA 15' | 8.40E+05 | 0.84 | 1.00E+06 | 1.48E+05 | 1.54 |
| 3. 1% DMSO 15' | 7.40E+05 | 0.84 | 8.81E+05 | 1.56E+05 | 1.35 |
| 4. 5% DMSO 15' | 1.08E+06 | 0.99 | 1.09E+06 | 1.70E+05 | 1.67 |
| 5. 10% DMSO 15' | 8.98E+05 | 0.9 | 9.97E+05 | 6.01E+04 | 1.53 |
| 6. 140 mM NaCl 15' | 7.10E+05 | 0.98 | 7.24E+05 | 7.07E+04 | 1.11 |
| 7. 500 mM NaCl 15' | 7.45E+05 | 0.98 | 7.60E+05 | 1.77E+04 | 1.17 |
| 8. 1M NaCl 15' | 7.13E+05 | 0.73 | 9.76E+05 | 1.13E+05 | 1.50 |
| 9. 1% DMSO + 140 mM NaCl 15' | 1.02E+06 | 1 | 1.02E+06 | 3.54E+03 | 1.56 |
| 10. 140 mM NaCl 15'/0.25% T 15' | 1.30E+06 | 0.84 | 1.55E+06 | 6.72E+04 | 2.38 |
| 11. 2% coll 30' | 6.25E+05 | 0.96 | 6.51E+05 | 1.41E+04 | 1.00 |
| 12. 2% coll 120' | 1.85E+06 | 0.79 | 2.34E+06 | 1.52E+05 | 3.59 |
| 13. 0.15% coll 23 hrs | 9.53E+05 | 0.87 | 1.09E+06 | 1.24E+05 | 1.68 |

TABLE 1-continued

| treatment | total n cells | weight cartilage (g) | total n cells/g | sd | normalized to #11 |
|---|---|---|---|---|---|

Cartilage was pretreated for 15 minutes (15') with trypsin-EDTA (T) 0.25%, Hyaluronidase (HA) 2 mg/ml in PBS, DMSO, NaCl or a combination of DMSO + NaCl (#9) or NaCl followed by trypsin-EDTA (#10). All experimental samples (1-10) were subsequently digested with 2% collagenase type II for 30 minutes. Controls were digested with 2% collagenase for 30 minutes or 120 minutes or overnight for 23 hours in 0.15% collagenase type II. Cell viability was between 80 and 95% for all groups.

The cell number results show that pretreatment of cartilage in all experimental groups results in a significantly higher cell yield after 30 minutes collagenase digestion compared to 30 minutes collagenase digestion alone. The results also show that the cell yield in group 1-5 and 8-10 is not significantly different or is even higher than overnight digestion (23 hrs) with 0.15% collagenase type II (table 1 #13). However, it is also shown that upon collagenase digestion with 2% collagenase type II for 2 hrs, the cell yield increased even more than with pretreatment (see also Example III).

Thus, it is concluded that with pretreatment of cartilage prior to collagenase digestion it is possible to increase the cell yield compared to collagenase digestion alone. Moreover, within 45 minutes similar or higher cell yield can be established by a combination of pretreatment and collagenase digestion at a higher concentration compared to a conventional 23 hrs digestion with 0.15% collagenase.

EXAMPLE III

Figure 3:
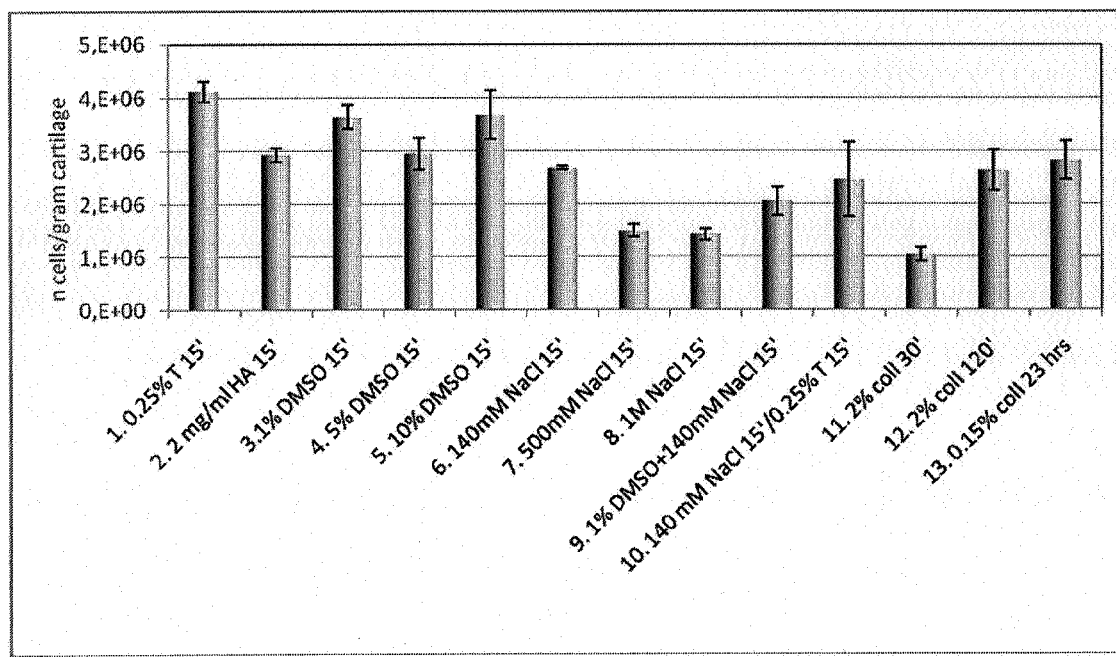
FIG. 3 is a graph showing the effect of a variety of digestion reaction conditions (shown in Table 2) on production of viable chondrocytes from cartilage.

Cartilage was retrieved from adult human cartilage biopsies (n=3) from the tibia. Cartilage was minced into ≤1 mm³ pieces. Approximately 1 gram of cartilage per group was transferred to 50 ml tubes and the exact weight of cartilage was determined (table 1). Chondrocytes were isolated by means of different pretreatment as described in Table 2, immediately followed by collagenase type II (Worthington) digestion for 120 minutes. The digested suspension was filtered through a 100 μm mesh nylon filter and the resulting cell suspension was centrifuged at 300 g for 10 minutes at 4° C. The cell pellet was washed twice with phosphate buffered saline (PBS) and finally resuspended in 1 ml PBS. The number of cells and the number of dead cells were determined with a Burker-Turk counting chamber. The results are summarized in Table 2 and FIG. 3.

TABLE 2

| treatment | total n cells | weight cartilage (g) | total n cells/g | sd | normalized against #12 |
|---|---|---|---|---|---|
| 1. 0.25% T 15' | 4.81E+06 | 1.17 | 4.11E+06 | 1.84E+05 | 1.56 |
| 2. 2 mg/ml HA 15' | 3.17E+06 | 1.08 | 2.94E+06 | 1.27E+05 | 1.11 |
| 3. 1% DMSO 15' | 3.88E+06 | 1.069 | 3.63E+06 | 2.26E+05 | 1.38 |
| 4. 5% DMSO 15' | 2.79E+06 | 0.95 | 2.94E+06 | 2.97E+05 | 1.11 |
| 5. 10% DMSO 15' | 3.38E+06 | 0.92 | 3.67E+06 | 4.53E+05 | 1.39 |
| 6. 140 mM NaCl 15' | 2.14E+06 | 0.8 | 2.68E+06 | 2.83E+04 | 1.01 |
| 7. 500 mM NaCl 15' | 1.49E+06 | 1 | 1.49E+06 | 1.13E+05 | 0.56 |
| 8. 1M NaCl 15' | 1.43E+06 | 1 | 1.43E+06 | 1.06E+05 | 0.54 |
| 9. 1% DMSO + 140 mM NaCl 15' | 2.03E+06 | 0.99 | 2.05E+06 | 2.69E+05 | 0.78 |
| 10. 140 mM NaCl 15'/0.25% T 15' | 2.62E+06 | 1.06 | 2.47E+06 | 7.00E+05 | 0.94 |
| 11. 2% coll 30' | 1.15E+06 | 1.11 | 1.03E+06 | 1.31E+05 | 0.39 |
| 12. 2% coll 120' | 2.69E+06 | 1.02 | 2.64E+06 | 3.82E+05 | 1.00 |
| 13. 0.15% coll 23 hrs | 3.58E+06 | 1.27 | 2.82E+06 | 3.68E+05 | 1.07 |

Cartilage was pretreated with trypsin-EDTA (T) 0.25%, Hyaluronidase (HA) 2 mg/ml in PBS, DMSO, NaCl or a combination of DMSO + NaCl (#9) or NaCl followed by trypsin-EDTA (#10). All experimental samples (1-10) were subsequently digested with 2% collagenase type II for 120 minutes. Controls were digested with 2% collagenase for 30 minutes or 120 minutes or overnight for 23 hours in 0.15% collagenase type II. Cell viability was between 80 and 88% for all groups.

Cell number results show that pretreatment of cartilage in all experimental groups, except #7 and #8, results in a significantly equal or higher cell yield after 120 minutes collagenase digestion compared to 120 minutes collagenase digestion alone. Pretreatment with 500 mM (#7) or 1M (#8) NaCl results in lower cell yield upon collagenase type II digestion. The results also show that the cell yield in group 1- is not significantly different or is even higher than overnight digestion (23 hrs) with 0.15% collagenase type II (table 1 #13).

Thus, it is concluded that pretreatment of cartilage with trypsine or DMSO prior to collagenase digestion makes it possible to increase the cell yield compared to collagenase digestion alone. Moreover, within 135 minutes similar of higher cell yield can be established by a combination of pretreatment of cartilage as described, followed by collagenase digestion at a higher concentration compared to a conventional 23 hrs digestion with 0.15% collagenase.

The invention claimed is:

1. A method to repair cartilage in a subject by implantation of chondrocytes comprising
    (a) subjecting a cartilage tissue sample from said subject to a single digestion enzyme or to more than one digestion enzyme sequentially or simultaneously, wherein the total period of time of exposure to the single digestion enzyme or to said more than one digestion enzymes is at least ten minutes and less than 2 hours to release said chondrocytes,
    (b) isolating the chondrocytes released in step (a) by separating the chondrocytes from the digestion enzyme or enzymes, thereby effectively ending the digestion process to obtain isolated chondrocytes, and directly implanting the chondrocytes into said subject;

wherein said method employs step (a) as the only treatment of said sample with any digestion enzyme.

2. The method according to claim 1, wherein the tissue sample is subjected to said enzymatic digestion for a period of less than 1 hour.

3. The method according to claim 1, wherein the cartilage tissue is articular cartilage.

4. The method according to claim 1, wherein at least one digestion enzyme is selected from the group consisting of collagenases, pronases, dispases, trypsins, hyaluronidases, chondroitinases, elastases, and heparitinases.

5. The method according to claim 4, wherein at least one digestion enzyme is collagenase type II.

6. The method according to claim 1, wherein the isolated chondrocytes are harvested by filtration, washing, centrifuging, and/or magnetic bead extraction.

7. The method according to claim 1, wherein the tissue sample is pretreated to increase extracellular matrix permeability prior to subjecting it to the enzymatic digestion of step (a) by increasing repulsive forces between glycosaminoglycans present in the extracellular matrix or by contacting the tissue sample with an acid, a base, dimethyl sulfoxide, glycerol, or cations.

8. The method according to claim 1, wherein the tissue sample is subjected to said enzymatic digestion for a period of 30 minutes or less.

9. The method according to claim 1, wherein the tissue sample is subjected to said enzymatic digestion for a period of 10 minutes.

10. A method for preparing chondrocytes from a cartilage tissue sample for use in implantation to repair cartilage comprising (a) pretreating the tissue sample with an acid, a base, DMSO or glycerol, directly followed by subjecting the tissue sample to a single digestion enzyme or to more than one digestion enzyme sequentially or simultaneously, wherein the total period of time of exposure to the single digestion enzyme or to said more than one digestion enzymes is at least ten minutes and less than 2 hours to release said chondrocytes, and (b) isolating the chondrocytes released in step (a) by separating the chondrocytes from the digestion enzyme or enzymes, thereby effectively ending the digestion process to obtain isolated chondrocytes, and wherein said method employs step (a) as the only treatment of said sample with any digestion enzyme.

11. The method according to claim 10, wherein the tissue sample is subjected to said enzymatic digestion for a period of less than 1 hour.

12. The method according to claim 10, wherein the tissue sample is subjected to said enzymatic digestion for a period of 30 minutes or less.

13. The method according to claim 10, wherein the tissue sample is subjected to said enzymatic digestion for a period of 10 minutes.

14. The method according to claim 10, wherein the cartilage tissue is articular cartilage.

15. The method according to claim 10, wherein at least one digestion enzyme is selected from the group consisting of collagenases, pronases, dispases, trypsins, hyaluronidases, chondroitinases, elastases, and heparitinases.

16. The method according to claim 10, wherein at least one digestion enzyme is collagenase type II.

17. The method according to claim 10, wherein the isolated chondrocytes are harvested by filtration, washing, centrifuging, and/or magnetic bead extraction.

* * * * *

UNITED STATES PATENT AND TRADEMARK OFFICE
CERTIFICATE OF CORRECTION

PATENT NO.       : 8,697,442 B2                                         Page 1 of 1
APPLICATION NO.  : 12/439145
DATED            : April 15, 2014
INVENTOR(S)      : Hendriks et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 330 days.

Signed and Sealed this

Twenty-ninth Day of September, 2015

Michelle K. Lee
*Director of the United States Patent and Trademark Office*